US009778159B2

(12) United States Patent
D'Antona et al.

(10) Patent No.: US 9,778,159 B2
(45) Date of Patent: Oct. 3, 2017

(54) SYSTEM AND METHOD FOR ASSESSING RHEOLOGICAL PROPERTIES OF GREASE

(71) Applicants: Egidio D'Antona, Utrecht (NL); Pieter Martin Lugt, Vianen (NL); Ileana Nedelcu, Nieuwegein (NL); Rihard Pasaribu, Nieuwegein (NL); Albertus Maria Van Der Vorst, Utrecht (NL)

(72) Inventors: Egidio D'Antona, Utrecht (NL); Pieter Martin Lugt, Vianen (NL); Ileana Nedelcu, Nieuwegein (NL); Rihard Pasaribu, Nieuwegein (NL); Albertus Maria Van Der Vorst, Utrecht (NL)

(73) Assignee: AKTIEBOLAGET SKF, Gothenburg (SE)

( * ) Notice: Subject to any disclaimer, the term of this patent is extended or adjusted under 35 U.S.C. 154(b) by 74 days.

(21) Appl. No.: 14/819,471

(22) Filed: Aug. 6, 2015

(65) Prior Publication Data
US 2016/0054214 A1 Feb. 25, 2016

(30) Foreign Application Priority Data

Aug. 21, 2014 (GB) .................................. 1414853.0

(51) Int. Cl.
G01N 11/02 (2006.01)
G01N 11/04 (2006.01)
G01N 11/00 (2006.01)

(52) U.S. Cl.
CPC ............. *G01N 11/02* (2013.01); *G01N 11/04* (2013.01); *G01N 2011/008* (2013.01)

(58) Field of Classification Search
CPC ... G01N 11/02; G01N 11/04; G01N 2011/008

USPC ........................................................ 73/54.43
See application file for complete search history.

(56) References Cited

U.S. PATENT DOCUMENTS

2003/0037601 A1\* 2/2003 Mansky ................. G01N 11/04
73/54.05
2013/0152674 A1\* 6/2013 Noordover ............... G01N 3/08
73/53.05

FOREIGN PATENT DOCUMENTS

| JP | S5855838 A | 4/1983 | |
| JP | 59143937 A | * 8/1984 | ............ G01N 11/00 |
| JP | S59143937 A | 8/1984 | |
| JP | S61223631 A | 10/1986 | |
| JP | H0324508 A | 2/1991 | |

(Continued)

*Primary Examiner* — Natalie Huls
*Assistant Examiner* — Monica S Young
(74) *Attorney, Agent, or Firm* — Bryan Peckjian; SKF USA Inc. Patent Dept.

(57) ABSTRACT

A system for investigating rheological properties of grease, the system including grease sample preparation arrangement for preparing a grease sample with a predetermined quantity of grease, at least two sample holder plates for holding the grease sample by sandwiching the grease sample between the sample holder plates, wherein at least one of the sample holder plates is transparent, and a loading system for generating a predetermined force acting on the grease sample sandwiched between the sample holder plates by pressing on the sample holder plates such that a spot formed by the grease sample on the sample holder plates is expanded. The loading system can include at least one transparent portion enabling a continuous observation of the expansion of the spot while the predetermined force is acting on the grease sample.

14 Claims, 3 Drawing Sheets

(56) References Cited

FOREIGN PATENT DOCUMENTS

| NL | WO 2011066455 A1 * | 6/2011 | ............... G01N 3/08 |
| RU | 2458243 C1 | 8/2012 | |

* cited by examiner

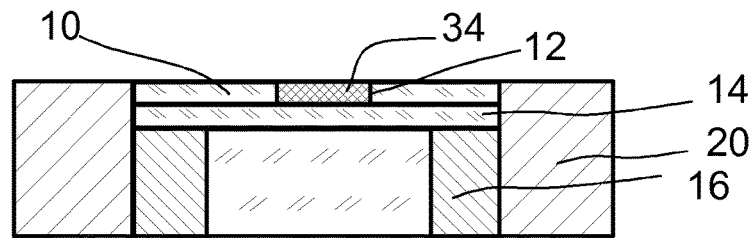
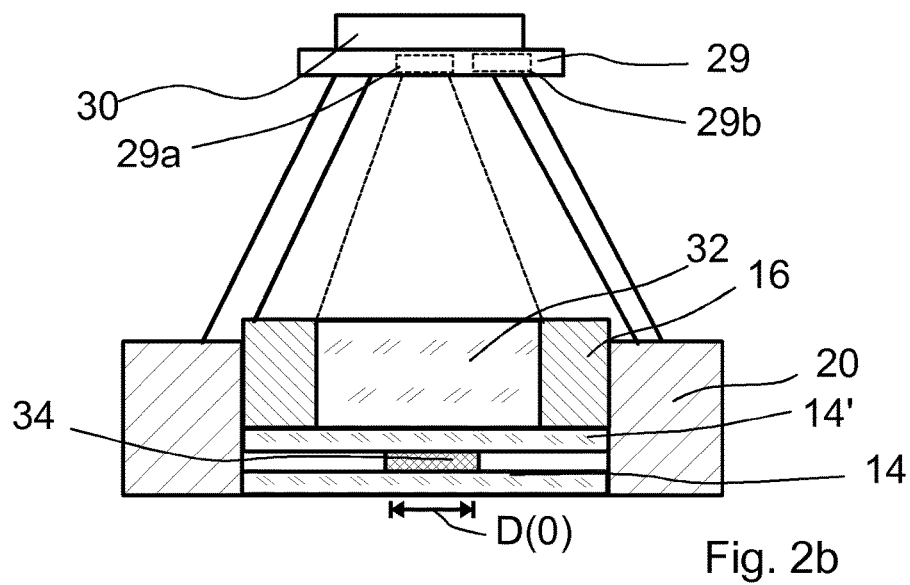
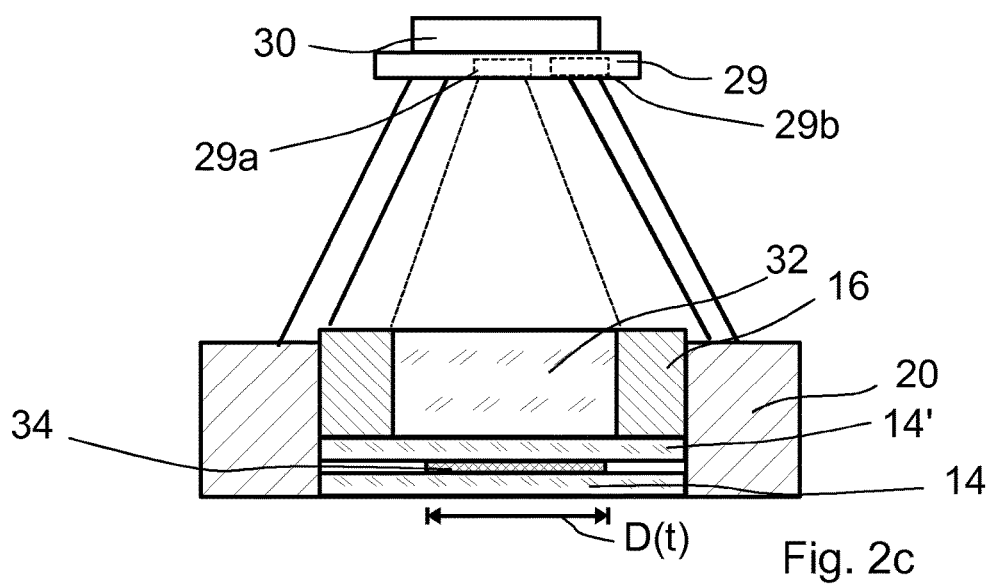

SYSTEM AND METHOD FOR ASSESSING RHEOLOGICAL PROPERTIES OF GREASE

CROSS REFERENCE TO RELATED APPLICATIONS

This is a Non-Provisional Patent Application, filed under the Paris Convention, claiming the benefit of Great Britain (GB) Patent Application Number 1414853.0, filed on 21 Aug. 2014 (21.08.2014), which is incorporated herein by reference in its entirety.

FIELD OF THE INVENTION

The invention relates to a system and to method for investigating rheological properties, in particular the pumpability of grease.

BACKGROUND OF THE INVENTION

System components which are critical for the system as a whole need reliable lubrication. Often, this is the case for bearings. It is known to employ automated lubrication systems including one or more grease pumps for this purpose. The choice of appropriate lubricants is crucial for the functioning of automated lubrication systems as it has to be made sure that the lubricant reaches its intended destination. Even if a satisfactory lubricant has been identified, ecological and economical demands as well as new developments in the field of tribology and rheology may require changing the type of lubricant employed.

However, many types of grease do not lend themselves to being pumped. The property "pumpability" is understood to refer to the behavior of lubricants when they are being pumped under the operating conditions to be anticipated.

Among the different types of lubricant, the rheological behavior of grease is particularly complex because grease is a multiphase product including base oils and one or more filler materials. Under certain loads and within its range of temperature application, grease exhibits the properties of a solid body, undergoes plastic strain and starts to flow like a fluid should the load reach the critical point, and regains solid-body properties after the removal of the stress.

One of the parameters frequently measured or indicated is the grease consistency classified according to a scale developed by the NLGI (National Lubricating Grease Institute). The scale is based on the degree of penetration achieved by allowing a standard cone to sink into the grease, which has been worked for 60 strokes in a grease worker, at a temperature of 25° C. for a period of 5 seconds. The depth of penetration is measured on a scale of 10-1 mm. The softer greases allow the cone to penetrate further into the grease, hence have a higher the penetration number. The test method is in accordance to ISO 2137.

Unfortunately, it is virtually impossible to determine the grease consistency using the ISO 2137 method under field conditions. The applicants have therefore developed grease test kit with a simple consistency test, wherein a grease sample with a predetermined volume and an initially circular shape is sandwiched between two circular glass plates and then pressed for 15 seconds by putting a weight on the stack. The grease spot expands due to the weight and the resulting diameter is measured and used as an indicator for the approximate NLGI number.

However, the grease consistency is not sufficient to determine the pumpability because different greases with the same consistency may have different pumpabilities.

The pumpability of grease is nowadays mainly determined in a laboratory using so-called ventmeters, wherein the grease is pressurized in a long tube and then released by opening a venting valve. The remaining pressure of the grease in the tube is used as an indicator for the pumpability and for recommendations for a minimum tube diameter required for using the tested grease in a lubrication system.

Ventmeters have the drawback of being complex and often not available on-site. However, manufacturers of bearings or of automated lubrication systems need to give recommendations regarding grease pumpability and regarding grease rheological properties at the customer site. When using grease with good pumpability, the quantities of lubricants required for the relubrication of bearings may be considerably reduced, which means that the consumption of lubricants will be lowered and the environmental burden will be lessened.

However, following the recommendations requires that simple system and method for checking the grease pumpability are available on-site.

SUMMARY OF THE INVENTION

The object of the invention is to provide a simple, portable system for measuring the rheological properties of a grease like apparent viscosity, flowability and/or pumpability.

The invention relates to a system for investigating the rheological properties, in particular the pumpability of grease, the system including grease sample preparation arrangement for preparing a grease sample with a predetermined quantity of grease, at least two sample holder plates for holding the grease sample by sandwiching the grease sample between the sample holder plates, wherein at least one of the sample holder plates is transparent, and loading system for generating a predetermined force acting on the grease sample sandwiched between the sample holder plates by pressing on the sample holder plates such that a spot formed by the grease sample on the sample holder plates is expanded.

In this context, the expression "investigating" may include observing assessing or measuring. As a universally recognized unit for the pumpability does not exist, qualitative as well as quantitative approaches shall be included. In addition to the pumpability, the investigated rheological properties may include apparent viscosity (rate at which the stain grows), flowablility or the yield stress (the ultimate size of the stain). Multiple of these parameters can also be determined using the system and the method according to the invention in a single experiment.

The invention proposes to provide the loading system with at least one transparent portion enabling a continuous observation of the expansion of the spot while the predetermined force is acting on the grease sample. The transparent portion in combination with the transparent sample holder plate enables a continuous observation of the spot expansion which can then be evaluated to obtain supplementary information on the rheological properties of the grease beyond its NLGI number.

The inventors have demonstrated that the dynamic expansion of the grease sample in a rheometer with a simple design having two plates sandwiching the sample is governed by the same relevant rheological parameters as the flow in ventmeters with pipe geometry and that the rheological parameters can be deduced from this dynamic expansion if it is observed. In other words, the results obtained with a device with pipe geometry can be translated into the results obtained with a device with the geometry according to the invention and vice versa.

Preferably, the loading system for generating the predetermined force is a weight. However, embodiments with springs for generating the predetermined force are possible.

In a preferred embodiment of the invention, the weight is entirely made of glass, wherein heavy metal parts may be embedded into the glass. Alternatively, the weight may have a metal body, e.g. of stainless steel, and further include a transparent window.

It is further proposed that the system comprises a frame for aligning the sample holder plates and the loading system, wherein the frame may in particular help to orient the weight horizontally. Further, the frame may be provided with lateral recesses with a diameter of 1-3 cm allowing the insertion of fingers to take the weight out of the frame after completion of the measurement or to put the components into the frame.

In a preferred embodiment of the invention, the system comprises a camera for recording the expansion of the spot and/or holding feature for fixing the camera at a predetermined distance from the grease sample. The holding feature may be used in combination with any camera, e.g. a camera of a mobile phone.

It is further proposed that the system comprises data processing system configured to determine a size of the spot for a plurality of points in time from the data recoded by the camera and to determine a pumpability parameter quantifying the pumpability of the grease sample based on the evolution of the size of the spot over time.

The data processing system may be realized as software of a personal computer or, preferably, as application software of a portable device such as a tablet computer or a mobile phone.

In a preferred embodiment of the invention, the data processing system is configured to calculate a spot diameter as a function of time and to determine the pumpability parameter based on a time derivative of the spot diameter.

Further, it is proposed that the system comprises a temperature controlling system for controlling the temperature of the grease sample. The temperature controlling system may be formed e.g. as a Peltier element with a battery or with a power supply combined with the power supply of the data processing system, e.g. an USB interface.

A further aspect of the invention relates to a method for determining the pumpability of grease by using a system as described herein, the method including the steps of preparing a grease sample with a predetermined quantity of grease, sandwiching the grease sample between two sample holder plates and exerting a predetermined load onto the grease sample such that a spot formed by the grease sample on the sample holder plates is expanded.

It is proposed that the method further comprises the steps of continuously observing the expansion of the grease sample via the transparent portion of the loading system and of deriving the grease pumpability from the evolution of the spot size of the grease sample over time.

The above embodiments of the invention as well as the appended claims and figures show multiple characterizing features of the invention in specific combinations. The skilled person will easily be able to consider further combinations or sub-combinations of these features in order to adapt the invention as defined in the claims to his or her specific needs.

BRIEF DESCRIPTION OF THE FIGURES

FIGS. 2a, 2b, and 2c illustrate steps of a method using the system according to FIG. 1 for measuring the pumpability of grease.

DETAILED DESCRIPTION OF THE EMBODIMENTS

Figure 1:
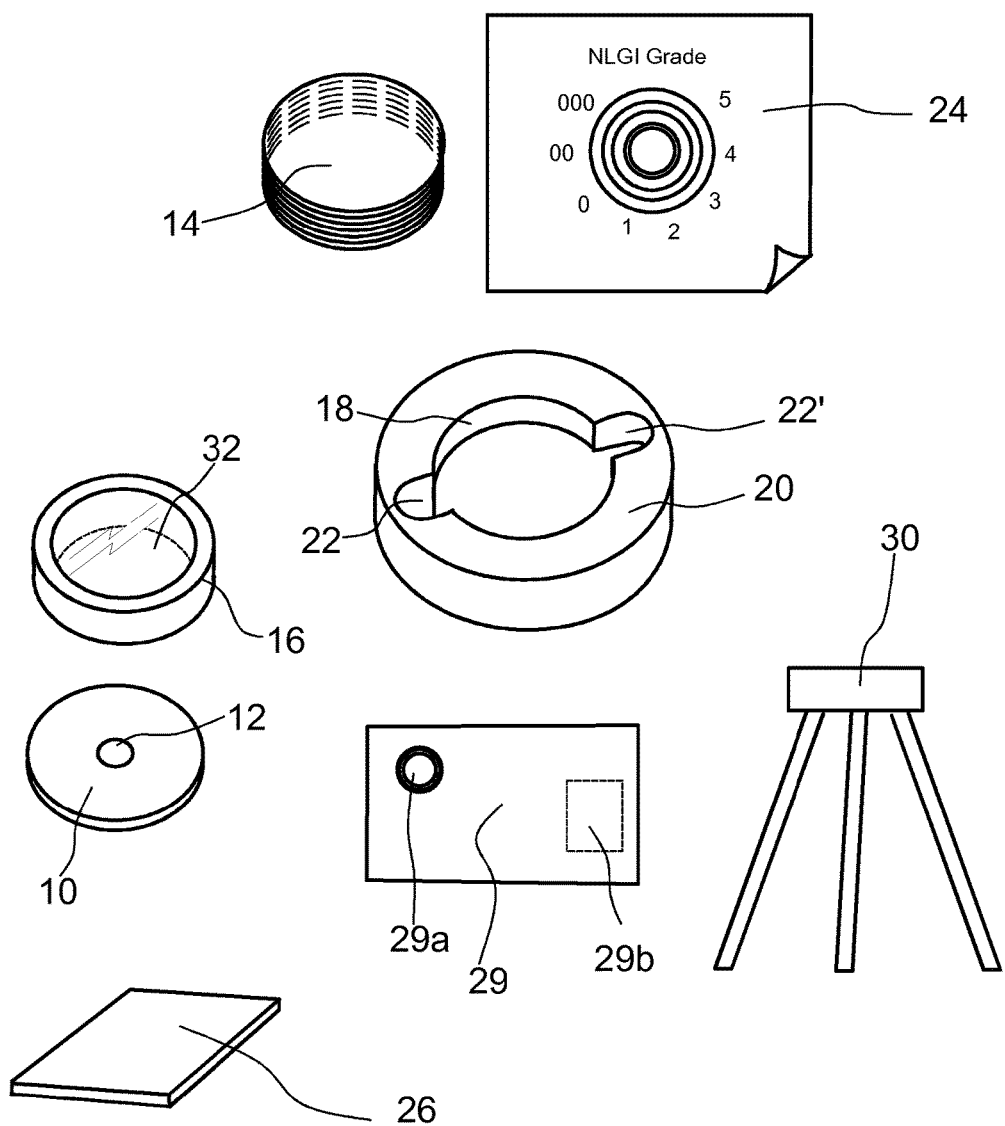
FIG. 1 illustrates the components system according to the invention.

FIG. 1 illustrates the components system for measuring the pumpability of grease according to the invention. The system includes glass mask 10 with a circular bore 12 as grease sample preparation arrangement for preparing a grease sample with a predetermined quantity of grease and a stack of sample holder plates 14 for holding the grease sample. The sample holder plates 14 are simple circular transparent glass plates.

Further, the system comprises a massive circular weight 16 as loading system for generating a predetermined force acting on the grease sample as explained in further detail below. The outer diameters of the weight 16, the glass mask 10 and the sample holder plates 14 are identical such that these components can be stacked on top of one another so as to form a perfectly cylindrical stack. The outer diameter of this stack corresponds to an inner diameter of a circular hole 18 formed in a frame 20 of the system. The hole 18 in the frame 20 has two lateral recesses 22, 22' on opposite sides allowing for inserting fingers for taking the weight 16, the sample holder plates 14 or the mask 10 into the frame 20 or for taking them out without moving the frame 20.

Further, the system comprises a scale sheet 24 with a printed calibrated scale of rings with predetermined diameters corresponding to different NLGI grades. The rings have different colors corresponding to colors of numbers indicating an NLGI grade printed on the scale sheet 24, respectively.

Further, the system comprises temperature controlling system 26 for controlling the temperature of the grease sample, wherein the temperature controlling system is formed as a Peltier element with a battery in the illustrated embodiment.

In addition to this, the system comprises a camera 29a and a data processing device 29b, which are both included in a Smartphone 29 in the embodiment illustrated. The Smartphone 29 has an application software installed, which records the expansion of the spot and determines a size of the spot for a plurality of points in time from the data recoded by its camera 29a and to determine a pumpability parameter quantifying the pumpability of the grease sample based on the evolution of the size of the spot over time.

Finally, the system includes a holding feature 30 or a pod for fixing the camera 29a at a predetermined distance from the grease sample.

According to the invention, the loading system formed as a weight 16 is provided a transparent portion 32 formed as a glass window enabling a continuous observation of the expansion of the spot while the predetermined force is acting on the grease sample.

A method for determining the pumpability of grease by using a system as described above for measuring the pumpability of grease is illustrated in FIG. 2a-2c.

FIG. 2a illustrates the step of preparing a grease sample 34 with a predetermined quantity of grease. The user makes sure that the components are clean, puts the frame 20 on a table and inserts the weight 16, a first sample holder plate 14 and the glass mask 10 into the frame 20 in this order. The central bore 12 of the glass mask 10 is then filled with the grease sample 34 to be investigated using a spatula and excessive grease protruding over the top surface of the mask 10 is taken off (not illustrated). The inner volume of the bore 12 in the glass mask 10 sets the volume of the grease sample 34. When the glass mask 10 is then taken off, a circular spot of grease with a diameter corresponding to the diameter of the bore and a thickness corresponding to the thickness of the mask 10 remains on the first sample holder 14.

The weight 16 and the sample holder 14 with the grease sample 34 are then taken out of the frame 20 and the frame 20 is placed on the scale sheet 24 such that the center of the concentric circles on the scale sheet is positioned in the center of the frame 20. If temperature control is desired, the scale sheet 24 with the frame 20 can be placed on the heating system 26.

As illustrated in FIG. 2b, the camera 29a is then mounted on the camera holder 30 and positioned over the center of the frame 20 such that a top view of the sample is taken. Then, the sample holder 14 with the grease sample 34 is placed in the frame 20 with the grease sample 34 on its top side, a second sample holder 14' is gently placed on top of the grease sample 34 such that the grease sample 34 is sandwiched between the two sample holder plates 14, 14' and finally the weight 16 is put on top of the stack while the camera 29a is recording. Upon placing the weight 16 on top of the stack, the user has to take care not to exert pressure on the weight 16 and not to obstruct the field of view of the camera 29a with his fingers.

While the weight 16 is lying on the uppermost sample holder plate 14, it exerts a predetermined load on the grease sample 34 in a vertical direction such that the outer diameter D(t) of the spot formed by the grease sample 34 on the sample holder plates 14 starts expanding with time until a maximum is reached The system with the expanded spot is illustrated in FIG. 2c. The expansion is continuously recorded by the camera 29a via the transparent portion 32 of the weight 16.

After having recorded the expansion, the data processing device 29b calibrates the measurement, e.g. by calculating an ellipticity and a diameter of the weight 16 or of the hole 18 in the frame 20 and by performing an image transformation and scaling on the images recorded by the camera 29a so as to achieve a circular shape with a predetermined diameter in the transformed image.

Then, the data processing device 29b extracts the diameter D(t) of the spot from the images taken by the camera 29a and stores the thus extracted diameters D(t) in a time series.

Figure 3:
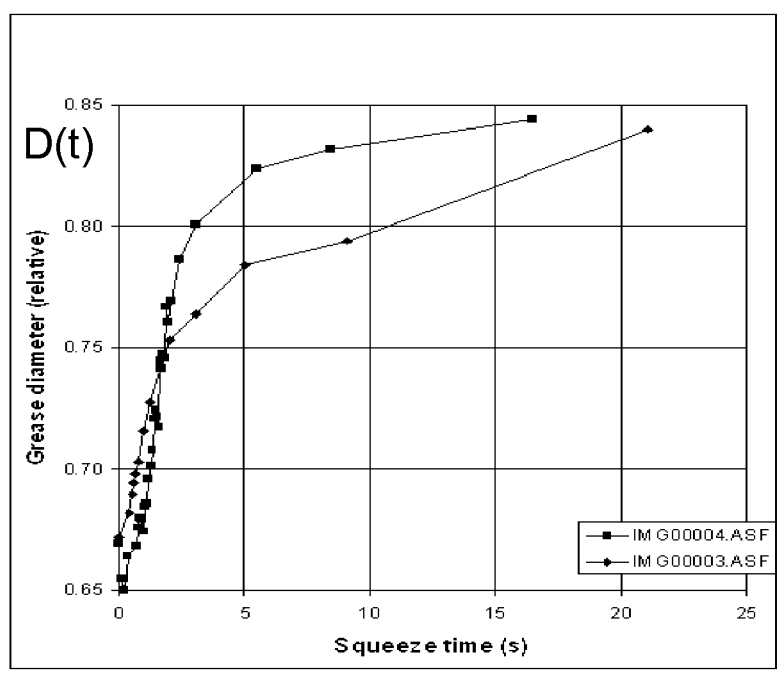
FIG. 3 is a graph showing the spot diameter of the grease sample for different types of grease.

FIG. 3 is a graph showing the spot diameter of the grease sample 34 for different types of grease. The graph with the rectangular points corresponds to a grease with a good pumpability with a steep initial increase and a relatively short time to reach its maximum, whereas the graph with the diamond-shaped points corresponds to a grease with lower pumpability. While the final spot diameter after 15 sec. measurement time is a value from which a good approximation for the NLGI consistency can be derived, the comparison between the curves in FIG. 3 shows that different greases with more or less the same NLGI consistency can display remarkable differences in their respective flow rates and behaviors in initial and intermediate phases of the expansion.

The data processing device 29b investigates these parameters in order to derive a parameter or information in the grease pumpability from the evolution of the spot size of the grease sample 34 over time. To this, end, the data processing device 29b may e.g. calculate the slope or higher time derivatives of the curve in the initial phase of the expansion or a constant describing how the spot diameter approaches its asymptotic value. The exact relation between the parameters of the curves and the pumpability can be determined heuristically using greases with pumpability values measured in a laboratory.

Based on this data on the grease rheological properties, the data processing device 29b displays recommendations regarding grease pumpability such as the pipe diameter and pipe length in addition to the NLGI consistency number.

It is noted that the automated investigation of the grease pumpability as described above does not require the scale sheet because it is possible to calibrate the camera 29a purely by image processing. However, the invention is not limited to automated evaluation and scale sheet may allow a human observer to watch the expansion and judge the pumpability. If the human judgment is considered sufficiently reliable, the camera 29a and the camera 29a holder as well as the data processing device 29b could be dispensed with.

The device is cheap to produce, is portable, and visual. It is fast and easy to use, simple and derived from an existing toolkit device for measuring grease consistency.

The invention claimed is:

1. A system for investigating rheological properties of grease, the system including:
   a grease sample preparation arrangement for preparing a grease sample with a predetermined quantity of grease;
   a first sample holder plate and a second sample holder plate for holding the grease sample by sandwiching the grease sample between the first and second sample holder plates, wherein at least one of the first and second sample holder plates is transparent; and
   a weight for generating a predetermined force acting on the grease sample sandwiched between the first and second sample holder plates by pressing on the first and second sample holder plates such that a spot formed by the grease sample on the first and second sample holder plates is expanded, the weight including at least one transparent portion enabling a continuous optical observation of the expansion of the spot while the predetermined force is acting on the grease sample, and
   further comprising a frame for aligning the first and second sample holder plates and the weight,
   wherein the frame is configured to receive the second sample holder plate and allow movement of the second sample plate in a first direction toward the first sample holder plate while substantially preventing movement of the second sample holder plate in a second direction perpendicular to the first direction.

2. The system according to claim 1, wherein the weight is made of glass.

3. The system according to claim 1, further comprising a camera for recording the expansion of the spot.

4. The system according to claim 3, further comprising a holding element for fixing the camera at a predetermined distance from the grease sample.

5. The system according to claim 3, further comprising a data processing system configured to determine a size of the spot for a plurality of points in time from the data recoded by the camera and to determine a rheological parameter the grease sample based on the evolution of the size of the diameter of the spot over time.

6. The system according to claim 5, wherein the data processing system is configured to calculate a spot diameter as a function of time and to determine a pumpability parameter quantifying the pumpability of the grease sample based on a time derivative of the spot diameter.

7. The system according to claim 1, further comprising a temperature controlling system for controlling the temperature of the grease sample.

8. A system for determining rheological properties of grease, the system including:
   a frame;
   a first sample holder plate configured to support a grease sample and a second sample holder plate having a first side and a second side, the first side being configured to rest on the grease sample to sandwich the grease sample between the first sample holder plate and the second sample holder plate, the first sample holder plate and/or the second sample holder plate being transparent; and
   a weight having a bottom configured to be supported by the second side of the second sample holder plate, the weight having a top and the weight having a transparent window through which light can pass from the bottom to the top,
   wherein the frame is configured to receive the second sample holder plate and allow movement of the second sample plate in a first direction toward the first sample holder plate while substantially preventing movement of the second sample holder plate in a second direction perpendicular to the first direction.

9. The system according to claim 8, wherein the frame is configured to receive the first sample holder plate and the weight and to allow movement of the weight in the first direction while substantially preventing movement of the first sample holder plate and the weight in the second direction.

10. The system according to claim 9, wherein the frame includes a circular opening for receiving the first sample holder plate and the second sample holder plate and the weight.

11. The system according to claim 10, further comprising:
    a camera configured to capture a succession of images of the grease sample through the window at a plurality of time points;
    a holder for fixing the camera at a predetermined distance from the grease sample; and
    a data processing system configured to determine from the succession of images a rheological parameter of the grease sample.

12. The system according to claim 8, wherein the window comprises glass.

13. A method for determining rheological properties of grease using the system according to claim 8, the method comprising:
    placing the grease sample on the first sample holder plate, the grease sample having a predetermined size and shape;
    placing the second sample holder plate on the grease sample;
    placing the weight on the second sample holder plate; and
    continuously observing an expansion of the grease sample through the window and deriving at least one rheological property of the grease sample from the expansion of the grease sample over time.

14. The method according to claim 13, wherein the continuously observing comprises capturing images with a camera.

* * * * *